United States Patent
Lu

(10) Patent No.: US 8,197,256 B2
(45) Date of Patent: Jun. 12, 2012

(54) FIBER OPTICS DENTAL POST

(75) Inventor: Luke Lu, Taipei (TW)

(73) Assignee: Taiwan Fiber Optics, Inc., Taipei (TW)

( * ) Notice: Subject to any disclaimer, the term of this patent is extended or adjusted under 35 U.S.C. 154(b) by 243 days.

(21) Appl. No.: 12/629,587

(22) Filed: Dec. 2, 2009

(65) Prior Publication Data

US 2011/0129788 A1 Jun. 2, 2011

(51) Int. Cl.
*A61C 5/02* (2006.01)
(52) U.S. Cl. ........................................ 433/220; 433/224
(58) Field of Classification Search .................. 433/220, 433/221, 224, 225
See application file for complete search history.

(56) References Cited

U.S. PATENT DOCUMENTS

| | | | | |
|---|---|---|---|---|
| 4,475,892 A | * | 10/1984 | Faunce | 433/212.1 |
| 5,074,792 A | * | 12/1991 | Bernadat | 433/220 |
| 5,328,372 A | * | 7/1994 | Reynaud et al. | 433/220 |
| 5,890,904 A | * | 4/1999 | Reynaud et al. | 433/220 |
| 5,915,970 A | * | 6/1999 | Sicurelli et al. | 433/220 |
| 5,919,044 A | * | 7/1999 | Sicurelli et al. | 433/220 |
| 5,989,032 A | * | 11/1999 | Reynaud et al. | 433/224 |
| 6,183,253 B1 | * | 2/2001 | Billet et al. | 433/81 |
| 6,186,791 B1 | * | 2/2001 | Karmaker et al. | 433/220 |
| 6,267,597 B1 | * | 7/2001 | Kim | 433/224 |
| 6,447,297 B1 | * | 9/2002 | Lopez et al. | 433/224 |
| 7,318,726 B2 | * | 1/2008 | Nordin | 433/224 |
| 7,488,175 B2 | * | 2/2009 | Karmaker et al. | 433/220 |

* cited by examiner

*Primary Examiner* — Ralph Lewis

(57) ABSTRACT

A fiber optics dental post includes a resin body and plural fiber optics center shafts; wherein the resin body includes an outer peripheral face, a receiving irradiation portion, and a bottom; each of the fiber optics center shafts pierces through and is fixed in the resin body, and has a receiving irradiation end and a light-guide irradiation end; each receiving irradiation end placed on the receiving irradiation portion of the resin body is used to receive the light irradiating on the receiving irradiation portion, and each light-guide irradiation end is respectively placed on the outer peripheral face and at the bottom of the resin body, thus the light received by each receiving irradiation end is propagated to the outer peripheral face and the bottom of the resin body through the light-guide irradiation end for irradiation, so as to effectively enhance the adhesion strength of the dental post.

10 Claims, 10 Drawing Sheets

FIBER OPTICS DENTAL POST

BACKGROUND OF THE INVENTION

1. Field of Invention

The present invention relates to a technical field of dental posts, more specifically to a fiber optics dental post with light-guide effect and opacity of X-ray.

2. Description of the Related Art

For a patient with serious caries or partial anodontia, dentists generally advise the patient to make a dental crown or bridge to recover the health of oral cavity and functions of a tooth; a dental crown or bridge adhered to the tooth of a patient is commonly referred to as fixed dental prosthesis; if a tooth is destroyed because of serious cariosity or injury, after root canal treatment, only fillings may not properly protect the tooth and recover functions thereof, and if the tooth accidentally bites a hard object, the tooth may be destroyed and need for extraction, thus the tooth must be covered with a dental crown.

Referring now to FIG. 12, a conventional denture generally includes a denture body 40 and a dental post 50; the upper part of the denture body 40 is a cover body 41, and the lower part is a support portion 42; more than one through holes are placed at the denture body 40 and are disposed through the cover body 41 and the support portion 42. The dental post 50 may be a metal dental post. After root canal treatment, bad enamel and dentin of the tooth are pared off, and the good enamel 60 and dentin thereof are maintained. Then, the denture body 40 is placed on the tooth, and the dental post 50 penetrates via the through hole of the denture body 40, thus the dental post 50 deeply penetrates within the root of the tooth.

Moreover, the denture body 40 and the dental post 50 are generally adhered to a tooth of a patient by way of a light curable adhesive, in which the adhesive is cured and adhesive by light irradiation, and the denture body 40 is firmly fixed on the tooth through the dental post 50 being adhered. However, the conventional dental post 50 without light-guide effect or with bad light-guide effect, even through light irradiation, the curing and adhesive effects of the light curable adhesive within the root of the tooth are not good, resulting in weak structural strength of the denture body 40. If the tooth accidentally bites a hard object, the denture body 40 may shed or be damaged, thus there is a need for improvement.

SUMMARY OF THE INVENTION

The technical feature of the problem-solving of the present invention includes to provide a fiber optics dental post including: a resin body and plural fiber optics center shafts. In which, the resin body includes an outer peripheral face, a receiving irradiation portion, and a bottom; each of the fiber optics center shafts pierces through and is fixed in the resin body for shaping, and has a receiving irradiation end and a light-guide irradiation end; each receiving irradiation end placed on the receiving irradiation portion of the resin body is used to receive the light irradiating on the receiving irradiation portion, and each light-guide irradiation end is respectively placed on the outer peripheral face and at the bottom of the resin body, thus the light received by each receiving irradiation end is propagated to the outer peripheral face and the bottom of the resin body through the light-guide irradiation end for irradiation.

The present invention can effectively enhance the light-guide effect of the dental post through the structural design of the fiber optics dental post. Thus, the received light can be propagated to the outer peripheral face and the bottom of the resin body through the light-guide irradiation end of the fiber optics dental post for irradiation, so as to effectively make the adhesive to be cured and adhesive through full irradiation by the light, and to effectively improve the structural bonding strength of the denture body and the adhesion strength of the dental post. As a result, the denture body will not easily shed off or be damaged. With the structural design of the fiber optics dental post, the present invention can effectively enhance the light-guide effect of the dental post and make the adhesive to be cured and adhesive through full irradiation by the light, and through the structural design of the resin body with opacity of X-ray irradiation, the structural strength of the fiber optics dental post is enhanced, so as to be useful and convenient in use.

DETAILED DESCRIPTION OF THE INVENTION

Figure 1:
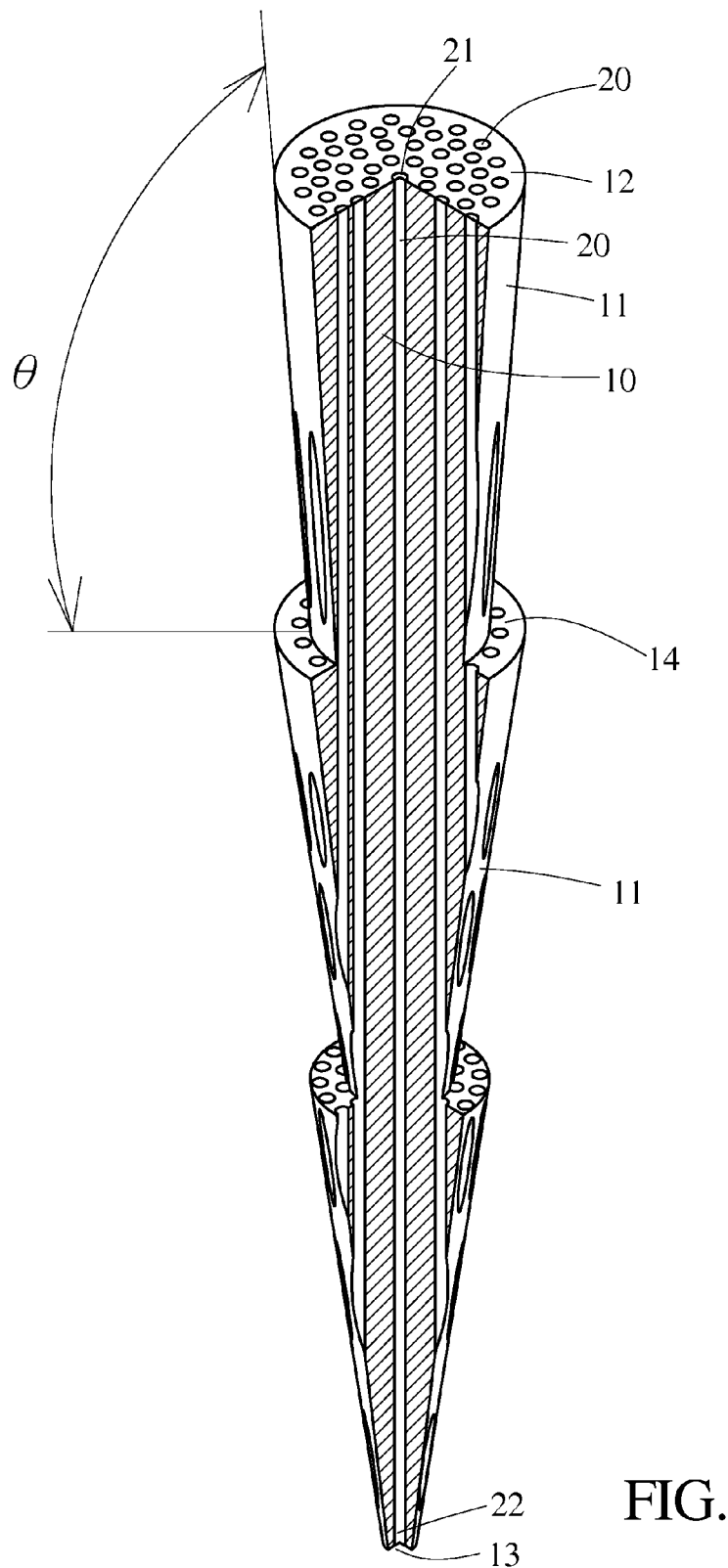
FIG. 1 is a schematic three-dimensional view of an embodiment according to the present invention.
Figure 2:
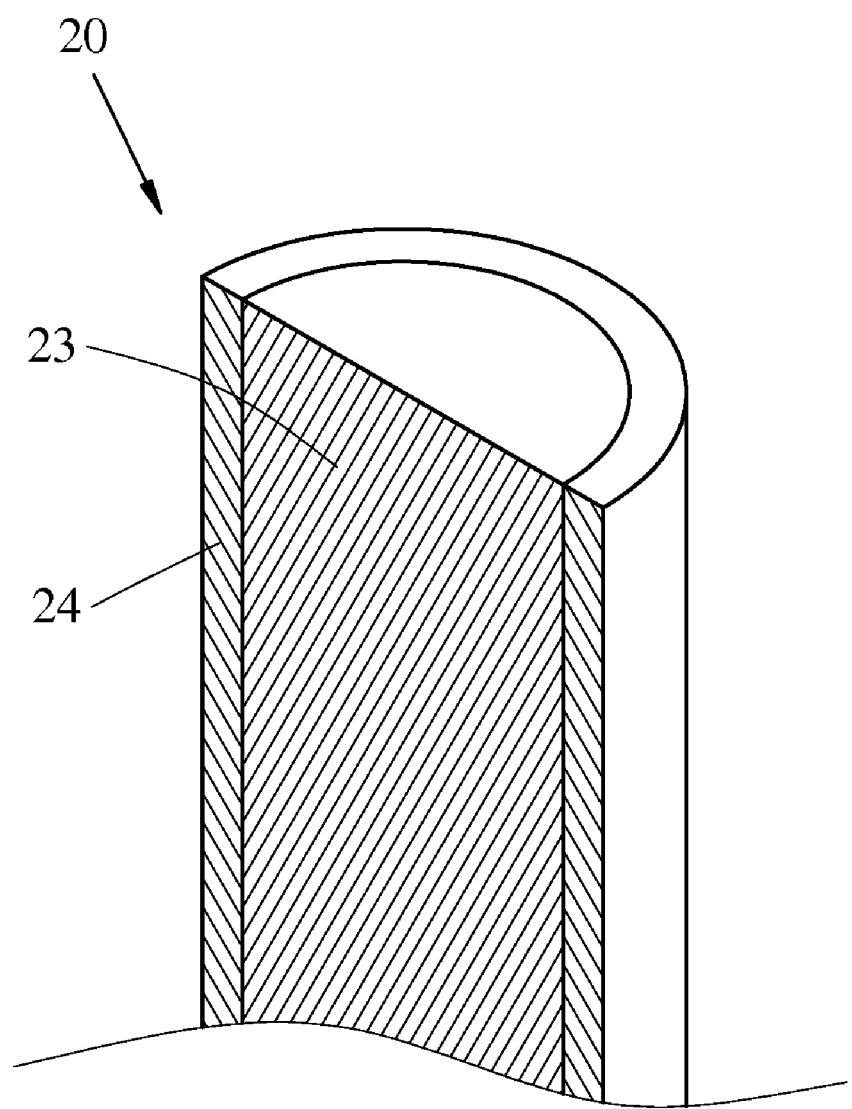
FIG. 2 is a schematic cross-sectional view of an embodiment of the fiber optics center shaft according to the present invention.

Referring to FIG. 1 to FIG. 11, the present invention provides a fiber optics dental post including: a resin body 10 and plural fiber optics center shafts 20. In which, the resin body 10 includes an outer peripheral face 11, a receiving irradiation portion 12, and a bottom 13; each of the fiber optics center shafts 20 pierces through and is fixed in the resin body 10 for shaping, and has a receiving irradiation end 21 and a light-guide irradiation end 22; each receiving irradiation end 21 placed on the receiving irradiation portion 12 of the resin body 10 is used to receive the light irradiating on the receiving irradiation portion 12, and each light-guide irradiation end 22 is respectively placed on the outer peripheral face 11 and at the bottom 13 of the resin body 10, thus the light received by each receiving irradiation end 21 is propagated to the outer peripheral face 11 and the bottom 13 of the resin body 10 through the light-guide irradiation end 22 for irradiation. In which, the weight percent of the plural fiber optics center shafts 20 in the fiber optics dental post is about 70%, and the weight percent of the resin body 10 in the fiber optics dental post is about 30%.

Figure 7:
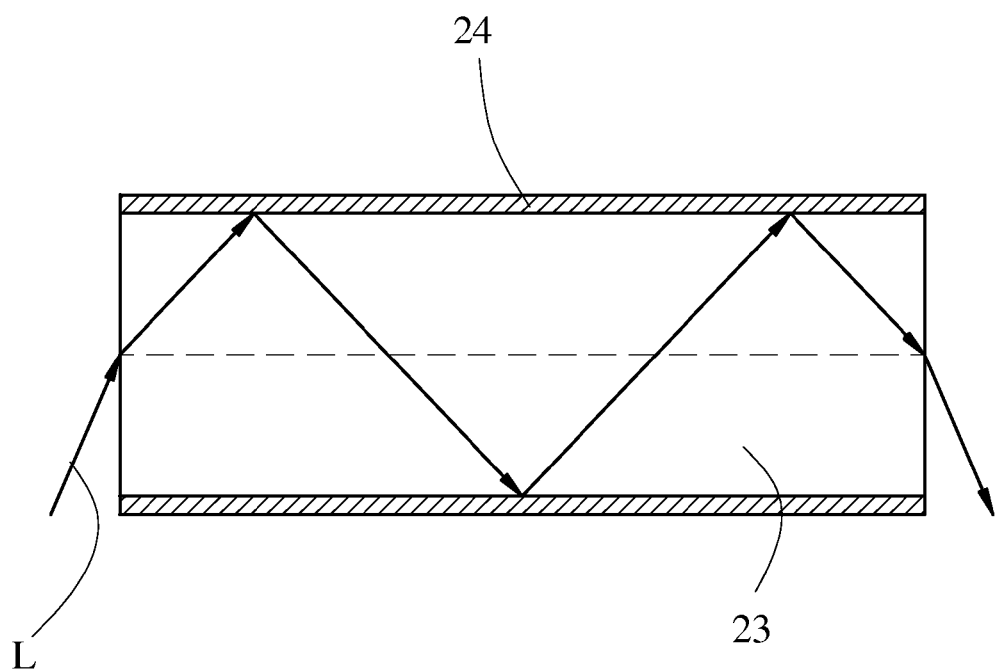
FIG. 7 is a schematic light transmission view of an embodiment of the fiber optics center shaft according to the present invention.

In which, each of the fiber optics center shafts 20 includes a fiber core layer 23 and a fiber clad layer 24, the fiber clad layer 24 coats and is fixed at the outside of the fiber core layer 23, and the fiber core layer 23 and the fiber clad layer 24 may be made of glass or plastic material; the refractive index of the fiber clad layer 24 is lower than that of the fiber core layer 23, so that light L can totally reflect along the inside of the fiber core layer 23 to achieve transmission, thus the light L emitted from such light source irradiates into each of the fiber optics center shafts 20 of the fiber core layer 23, and because of the fiber core layer 23 coated with the fiber clad layer 24 with higher refractive index, the light L irradiated inside is transmitted within the fiber core layer 23 (as shown in FIG. 7), so as to achieve the purpose of transmitting the light L by the fiber optics center shafts 20.

In which, there are plural stepped ring edges 14 further placed on the outer peripheral face 11 of the resin body 10.

Figure 3:
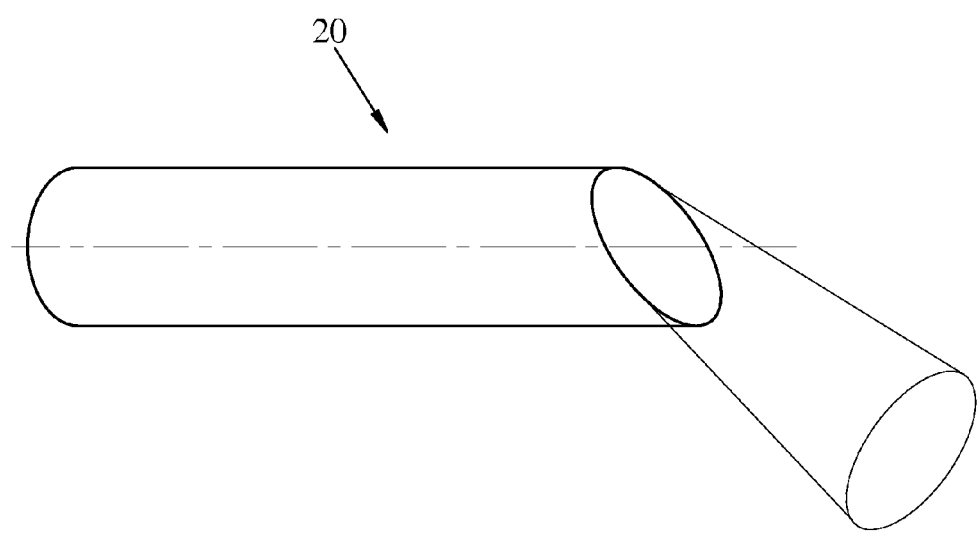
FIG. 3 is a schematic light propagation view of an embodiment of the fiber optics center shaft according to the present invention.
Figure 4:
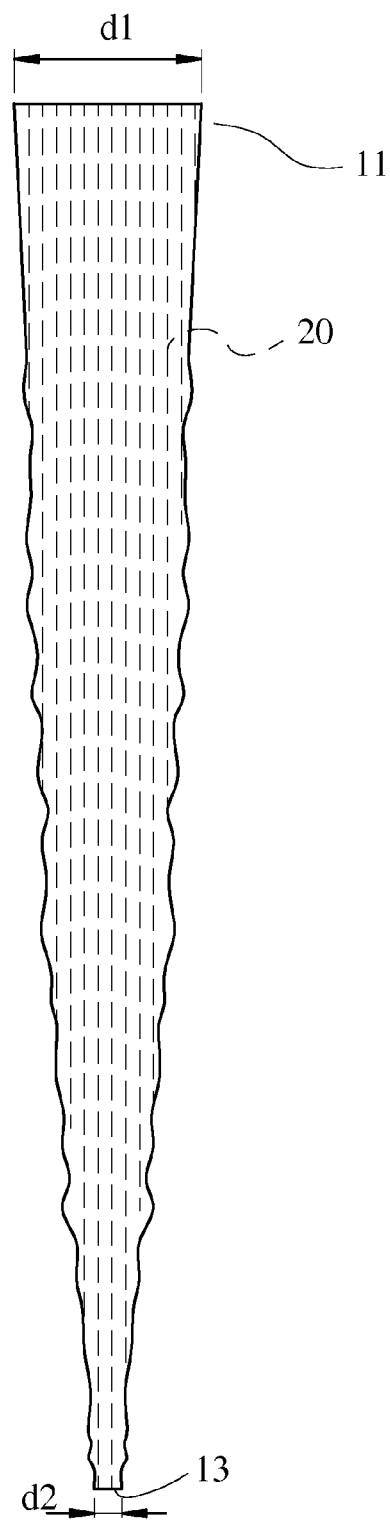
FIG. 4 is a schematic side view of another embodiment according to the present invention.
Figure 5:
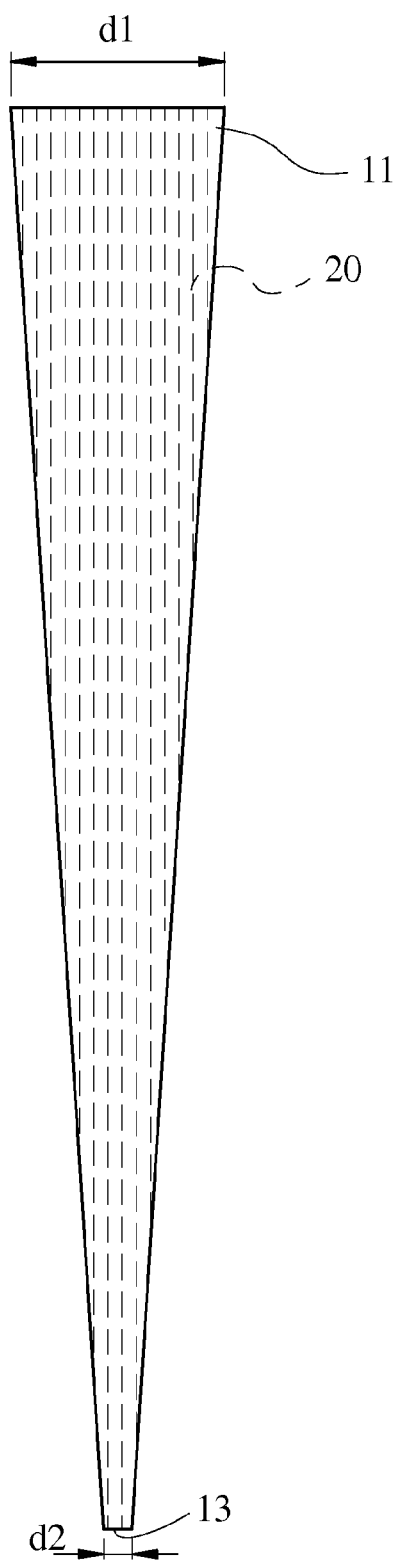
FIG. 5 is a schematic side view of a still embodiment according to the present invention.
Figure 6:
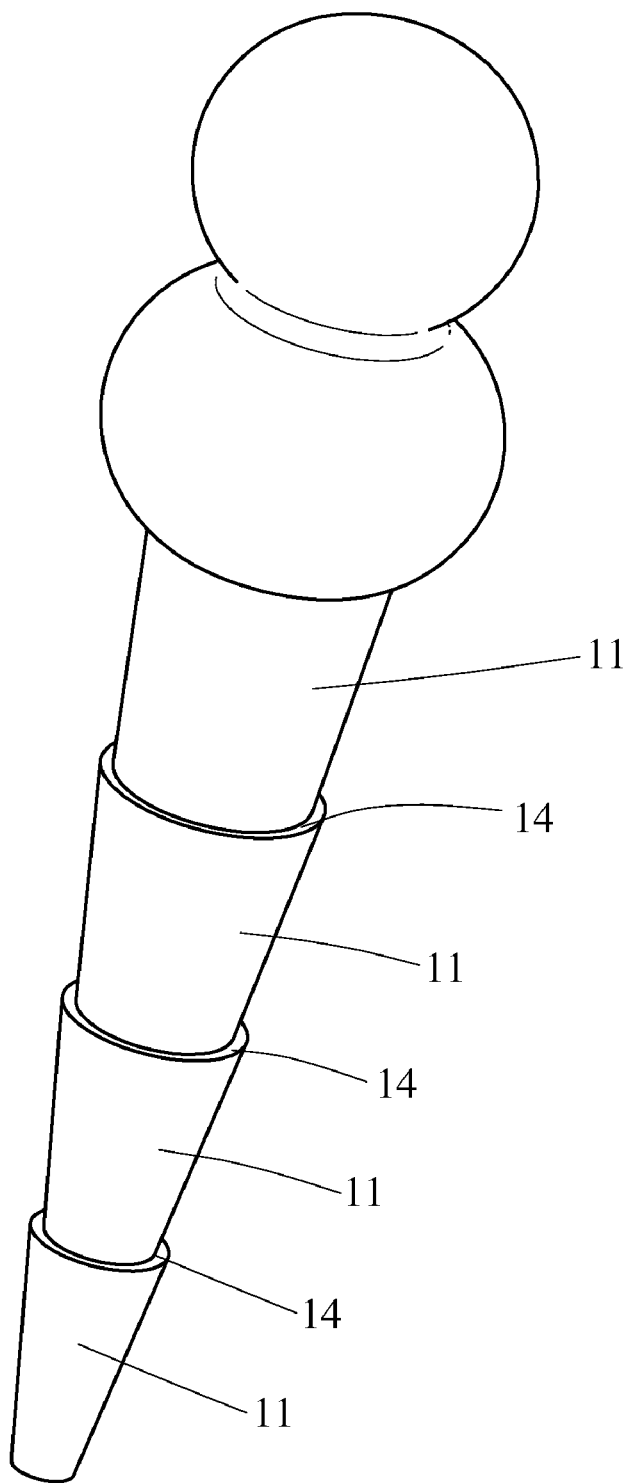
FIG. 6 is a schematic side view of a yet embodiment according to the present invention.

In which, each of the stepped ring edges 14 and the outer peripheral face 11 of the resin body 10 form an included angle θ, and the included angle θ may be an acute angle. Referring now to FIG. 3, which shows the irradiation direction of the light transmitted by the fiber optics, comparing with FIG. 1, the light irradiates from the outer peripheral face 11 of the dental post may further illuminate each of the fiber optics center shafts 20 on the stepped ring edges 14, thus, the whole dental post illuminates, so as to effectively enhance the light-guide effect of the dental post. Further, it effectively makes the light curable adhesive be fully cured and adhesive through full irradiation by the light, and to effectively strengthen the adhesion strength of the dental post.

In which, each of the stepped ring edges 14 is equidistantly placed to another one on the outer peripheral face 11 of the resin body 10.

In which, the outer peripheral face 11 of the resin body 10 is further coated with a light curable adhesive, through the light-guide effect of the fiber optics dental post, the light curable adhesive is fully cured and adhesive through full irradiation by the light, so as to effectively strengthen the adhesion strength of the dental post.

In which, the receiving irradiation portion 12 has a first caliber d1, the bottom 13 has a second caliber d2, and the first caliber d1 is bigger than the second caliber d2.

Figure 8:
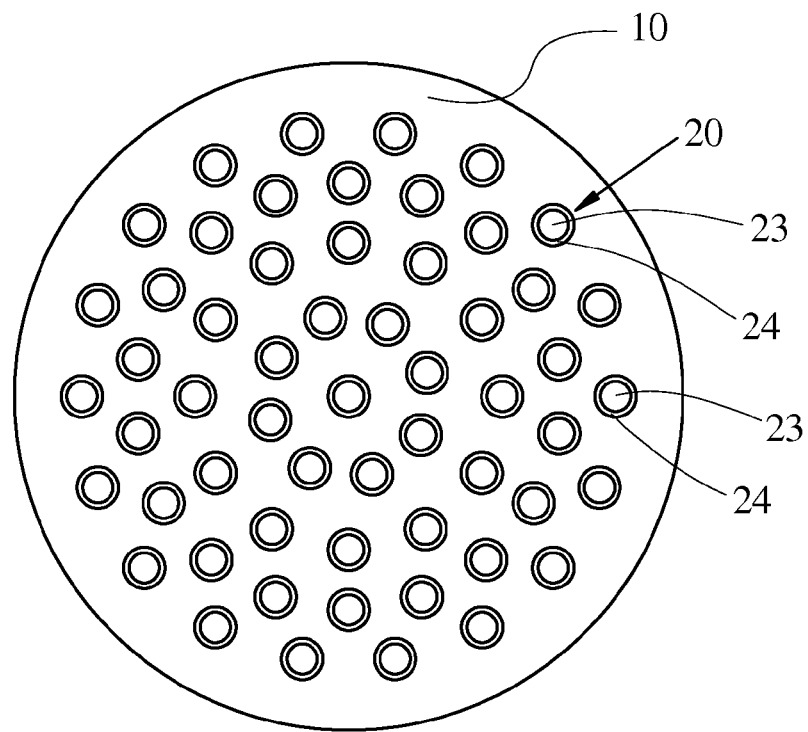
FIG. 8 is a schematic top view of an embodiment of the single fiber design according to the present invention.
Figure 9:
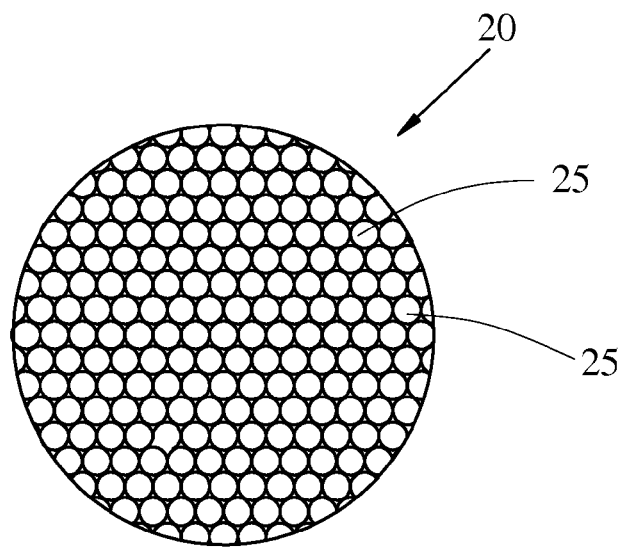
FIG. 9 is a schematic enlarged partial top view of an embodiment of the multi-fiber design according to the present invention.
Figure 10:
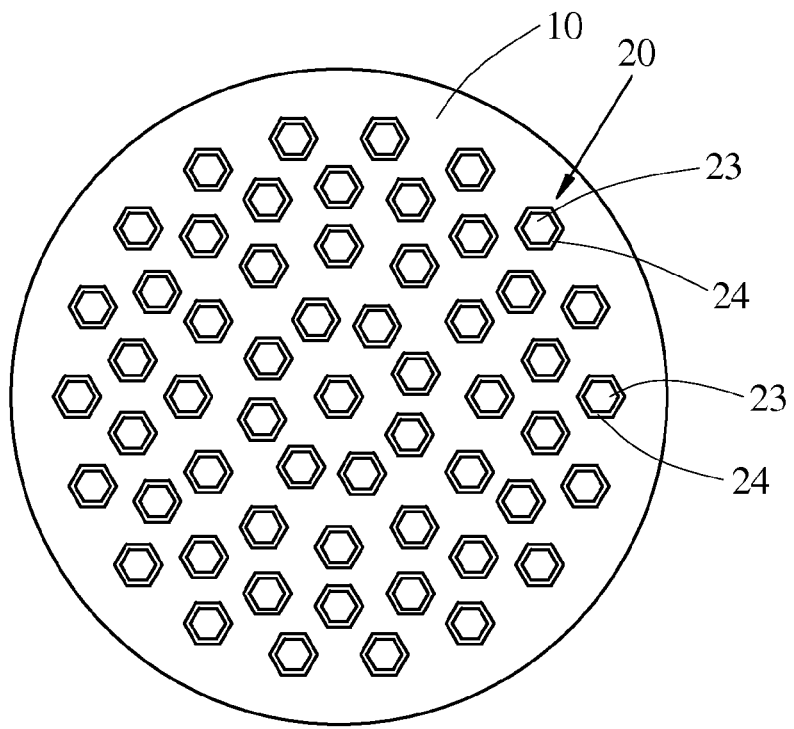
FIG. 10 is a schematic top view of an embodiment of the hexagonal single fiber design according to the present invention.
Figure 11:
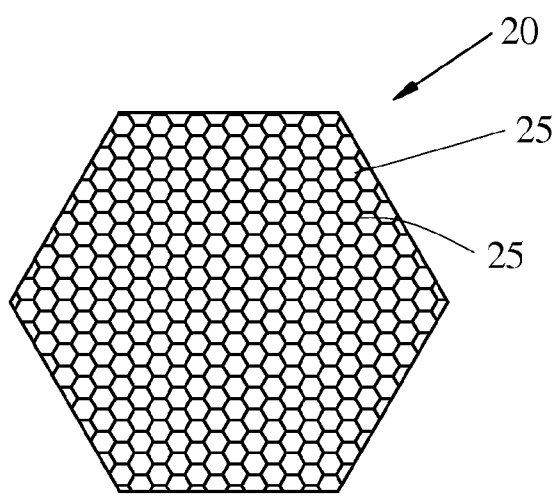
FIG. 11 is a schematic enlarged partial top view of an embodiment of the hexagonal multi-fiber design according to the present invention.
Figure 12:
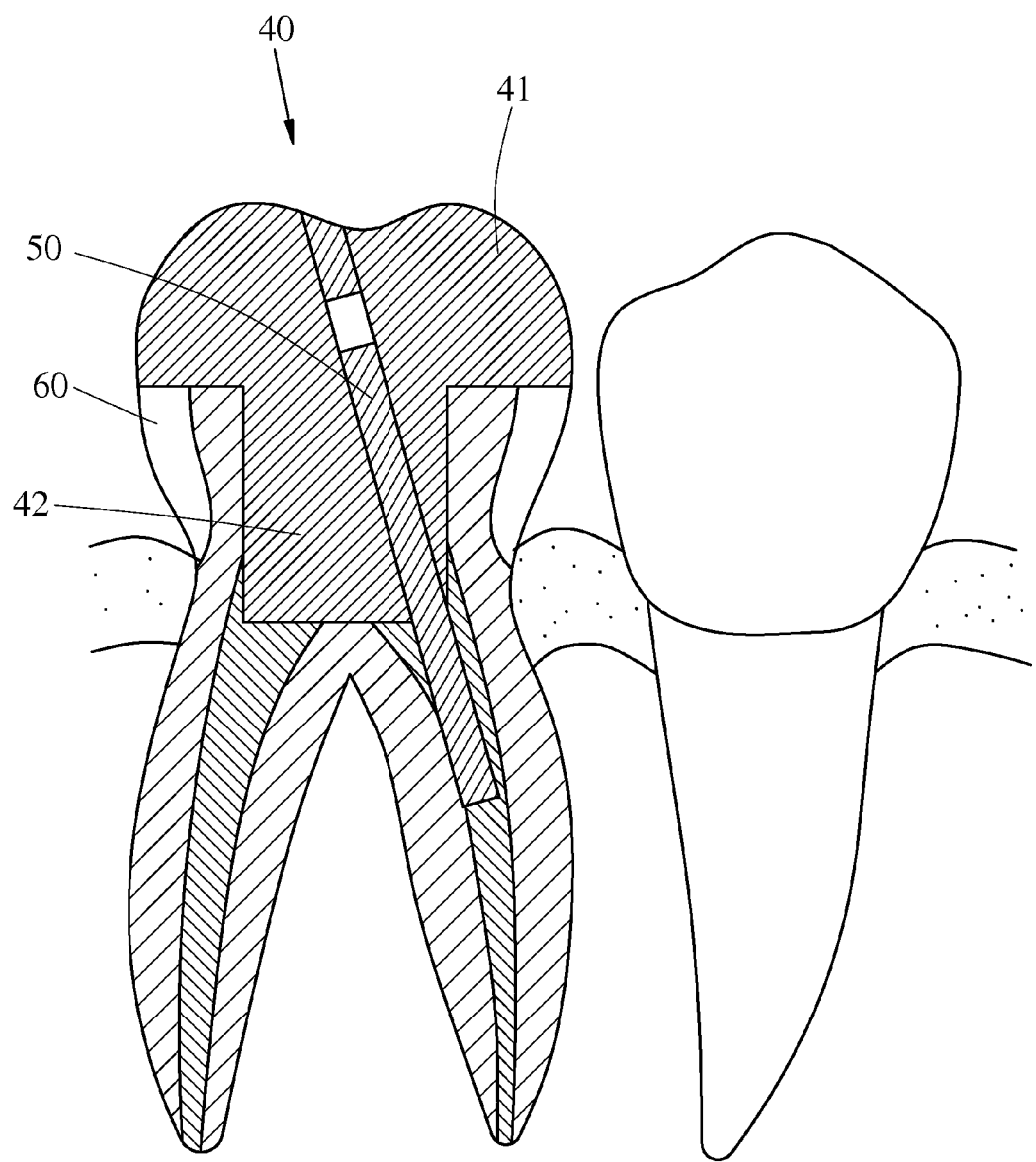
FIG. 12 is a schematic cross-sectional view showing the use state of a conventional dental post.

According to the present invention, a single fiber design (as shown in FIG. 8 and FIG. 10) or a multi-fiber design (as shown in FIG. 9 and FIG. 11) is adopted for the fiber optics center shafts 20 of the dental post, wherein the multi-fiber design means that each of the fiber optics center shafts 20 may be composed of a number of unit fiber optics 25, so as to make the irradiation effect more uniform.

In which, the cross-section of each unit fiber optics 25 is round in shape.

In which, the cross-section of each unit fiber optics 25 is a hexagonal shape, and the structural strength of the unit fiber optics 25 with hexagonal shape is better.

To sum up, first, the present invention can effectively enhance the light-guide effect of the dental post through the structural design of the fiber optics dental post, thus the received light can be propagated to the outer peripheral face and the bottom of the resin body through the light-guide irradiation end of the fiber optics dental post for irradiation, so as to effectively make the adhesive to be cured and adhesive through full irradiation by the light, and to effectively improve the structural bonding strength of the denture body and the adhesion strength of the dental post. As a result, the denture body will not easily shed off from the tooth or be damaged. Moreover, with the structural design of the fiber optics dental post, the present invention can effectively enhance the light-guide effect of the dental post and make the adhesive to be cured and adhesive through full irradiation by the light. In addition, through the structural design of the resin body with opacity of X-ray irradiation, the structural strength of the fiber optics dental post is enhanced, so as to be useful and convenient in use.

What is claimed is:

1. A fiber optics dental post, including:
   a resin body, in which the resin body includes an outer peripheral face, a receiving irradiation portion, and a bottom; and
   a plurality of fiber optics center shafts, in which each of the fiber optics center shafts pierces through and is fixed in the resin body for shaping, and has a receiving irradiation end and a light-guide irradiation end; each receiving irradiation end placed on the receiving irradiation portion of the resin body is used to receive a light irradiating on the receiving irradiation portion, and each light-guide irradiation end is respectively placed on the outer peripheral face and at the bottom of the resin body, thus the light received by each receiving irradiation end is propagated to the outer peripheral face and the bottom of the resin body through the light-guide irradiation end for irradiation;
   a plurality of stepped ring edges having a plurality of exposed fibers, said stepped ring edges are disposed on the outer peripheral face of the resin body; and;
   wherein at least one of the light-guide irradiation end has an opening, wherein said opening is oblique so as to propagate the light to at least some of the exposed fibers on the stepped ring edges.

2. The fiber optics dental post as claimed in claim 1, wherein each of the fiber optics center shafts includes a fiber core layer and a fiber clad layer, and the fiber clad layer coats and is fixed at the outside of the fiber core layer.

3. The fiber optics dental post as claimed in claim 1, wherein each of the stepped ring edges and the outer peripheral face of the resin body form an included angle, which is an acute angle.

4. The fiber optics dental post as claimed in claim 1, wherein each of the stepped ring edges is equidistantly placed to another one on the outer peripheral face of the resin body.

5. The fiber optics dental post as claimed in claim 1, wherein the receiving irradiation portion has a first caliber, the bottom has a second caliber, and the first caliber is bigger than the second caliber.

6. The fiber optics dental post as claimed in claim 1, wherein each of the fiber optics center shafts is composed of plural unit fiber optics.

7. The fiber optics dental post as claimed in claim 6, wherein the cross-section of each unit fiber optics is a round shape.

8. The fiber optics dental post as claimed in claim 6, wherein the cross-section of each unit fiber optics is a hexagonal shape.

9. The fiber optics dental post as claimed in claim 1, wherein the weight percent of the plural fiber optics center shaft in the whole fiber optics dental post is 70%.

10. The fiber optics dental post as claimed in claim 1, wherein the weight percent of the resin body in the whole fiber optics dental post is 30%.

\* \* \* \* \*